US00PP29410P2

(12) United States Plant Patent
Braeunig

(10) Patent No.: US PP29,410 P2
(45) Date of Patent: Jun. 19, 2018

(54) PHLOX PLANT NAMED 'FLORPHFABV'

(50) Latin Name: *Phlox subulata*
Varietal Denomination: Florphfabv

(71) Applicant: Florensis B.V., Hendrik-Ido-Ambacht (NL)

(72) Inventor: Tobias M. Braeunig, Quendlinburg (DE)

(73) Assignee: Florensis B.V., Hendrik-Ido-Ambacht (NL)

( * ) Notice: Subject to any disclaimer, the term of this patent is extended or adjusted under 35 U.S.C. 154(b) by 0 days. days.

(21) Appl. No.: 15/731,495

(22) Filed: Jun. 19, 2017

(51) Int. Cl.
*A01H 5/02* (2018.01)

(52) U.S. Cl.
USPC ..... Plt./320
CPC ..... *A01H 5/02* (2013.01)

(58) Field of Classification Search
USPC ..... Plt./320
CPC ..... A01H 5/02
See application file for complete search history.

*Primary Examiner* — Kent L Bell
(74) *Attorney, Agent, or Firm* — Audrey Charles

(57) ABSTRACT

A new and distinct cultivar of *Phlox* plant named 'Florphfabv', characterized by its light violet-blue colored flowers, dark green-colored foliage, and moderately vigorous, mounded-spreading growth habit, is disclosed.

1 Drawing Sheet

Latin name of genus and species of plant claimed: *Phlox subulata.*

Variety denomination: 'Florphfabv'.

BACKGROUND OF THE INVENTION

The present invention relates to a new and distinct cultivar of *Phlox* plant botanically known as *Phlox subulata* and hereinafter referred to by the cultivar name 'Florphfabv'.

The new cultivar originated in a controlled breeding program in Quedlinburg, Germany during April 2008. The objective of the breeding program was the development of *Phlox* cultivars with increased cold tolerance and blue-colored flowers.

The new *Phlox* cultivar is the result of open-pollination. The female (seed) parent of the new cultivar is 'G.F. Wilson', also known as 'Lilacina', not patented, characterized by its light lavender-blue colored flowers, medium green-colored foliage, and vigorous, mounded growth habit. The male (pollen) parent of the new cultivar is unknown. The new cultivar was discovered and selected as a single flowering plant within the progeny of the above stated open-pollination during April 2009 in a controlled environment in Quedlinburg, Germany.

Asexual reproduction of the new cultivar by terminal stem cuttings since April 2009 in Quedlinburg, Germany has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Florphfabv' as a new and distinct cultivar of *Phlox* plant:

1. Light violet-blue colored flowers;
2. Dark green-colored foliage; and

3. Moderately vigorous, mounded-spreading growth habit.

Plants of the new cultivar differ from plants of the female parent primarily in flower color and growth vigor.

Of the many commercially available *Phlox* cultivars, the most similar in comparison to the new cultivar is Early Spring Blue 'Barsixtynine', U.S. Plant patent application Ser. No. 13/136,380, now abandoned. However, in comparison, plants of the new cultivar differ from plants of 'Barsixtynine' in at least the following characteristics:

1. Plants of the new cultivar have a slightly lighter flower color with darker colored spots at the corolla tube opening than plants of 'Barsixtynine';
2. Plants of the new cultivar have a darker colored corolla tube than plants of 'Barsixtynine'; and
3. Plants of the new cultivar have smaller leaves than plants of 'Barsixtynine'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Florphfabv'. The plants were approximately 10 months old and were grown in 13 cm pots for approximately 9 months in an outdoor nursery location in Hendrik-Ido-Ambacht, The Netherlands.

DETAILED BOTANICAL DESCRIPTION

Figure 1:
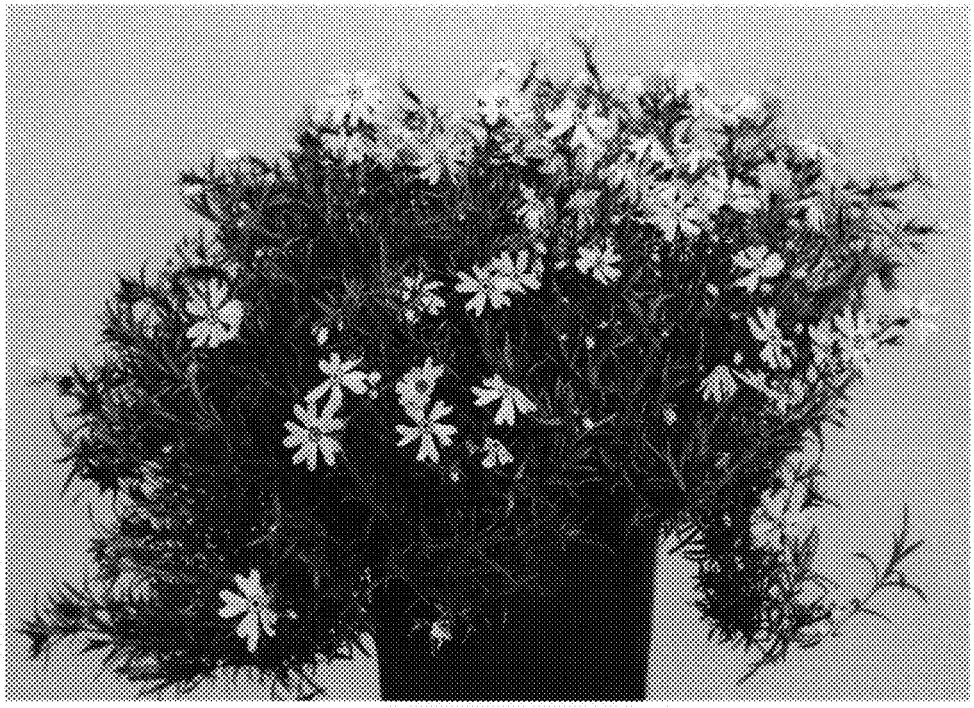
FIG. 1 illustrates a side view of the overall growth and flowering habit of 'Florphfabv'.
Figure 2:
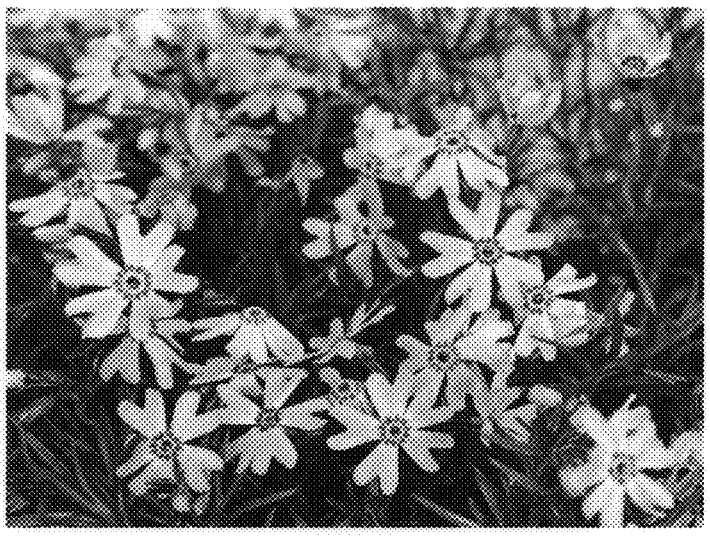
FIG. 2 illustrates a close-up view of the flowers of 'Florphfabv'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in April 2017 under natural light conditions in Boskoop, The Netherlands.

The following descriptions and measurements describe approximately 10-month old plants produced from cuttings from stock plants and grown in an outdoor nursery location in Hendrik-Ido-Ambacht, The Netherlands under conditions comparable to those used in commercial practice. The plants were grown in 13 cm pots utilizing a soilless growth medium for approximately 9 months. During this period the maximum temperatures ranged from 92° F. to 68° F. (33.3° C. to 20° C.) and the minimum temperatures ranged from 19° F. to 29° F. (−7.2° C. to −1.7° C.). Measurements and numerical values represent averages of typical plants.

Botanical classification: *Phlox subulata* cultivar Florphfabv.

Parentage:

*Female parent.*—'G.F. Wilson', also known as 'Lilacina', not patented.

*Male parent.*—Unknown.

Propagation:

*Type cutting.*—Terminal stem.

*Time to initiate roots.*—Approximately 12 to 14 days.

*Time to produce a rooted cutting.*—Approximately 42 to 49 days.

*Root description.*—Slightly fibrous, non-fleshy, thin, 159C in color.

*Rooting habit.*—Freely branched, dense.

Plant description:

*Commercial crop time.*—Approximately 5 to 6 months from a rooted cutting to finish in a 13 cm pot.

*Growth habit and general appearance.*—Herbaceous perennial, moderately vigorous, mounded-spreading habit.

*Hardiness.*—USDA Zone 4a (−30° F. to −25° F./−34.4° C. to −31.7° C.).

*Size.*—Height: Approximately 13.4 cm. Width: Approximately 38.2 cm.

*Branching habit.*—Low to moderate basal branching.

*Branch.*—Quantity: Approximately 18. Shape: Rounded. Strength: Strong. Length to base of inflorescence: Approximately 9.4 cm. Diameter: Approximately 2.0 mm. Length of central internode: Approximately 9.0 mm. Texture: Glabrous. Color of young stems: 184B. Color of mature stems: 145A, transitioning to 197D with age.

Foliage description:

*General description.*—Quantity of leaves per main branch: Approximately 22. Fragrance: None. Form: Simple. Arrangement: Opposite.

*Leaves.*—Shape: Narrowly lanceolate. Margin: Entire, ciliate. Apex: Narrowly acute. Base: Broadly cuneate, sessile. Venation pattern: Pinnate. Length of mature leaf: Approximately 2.1 cm. Width of mature leaf: Approximately 2.0 mm. Texture of upper surface: Glabrous. Texture of lower surface: Glabrous. Color of upper surface of young foliage: 144A with venation of 145C to 145D. Color of lower surface of young foliage: 144A with venation of 146D. Color of upper surface of mature foliage: NN137A with venation of NN137A, occasionally tinted with 187A. Color of lower surface of mature foliage: 144A with venation of 146D, occasionally tinted with 187A.

Flowering description:

*Flowering habit.*—'Florphfabv' is freely flowering under outdoor growing conditions blooming in early spring.

*Lastingness of individual flower on the plant.*—Approximately 7 to 10 days.

Inflorescence description:

*General Description.*—Type: Cyme, self-cleaning. Quantity per plant: Approximately 700. Fragrance: Moderately sweet. Height: Approximately 4.1 cm. Width: Approximately 4.0 cm. Quantity of fully open flowers per inflorescence: Approximately 3.

*Peduncle.*—Strength: Strong. Aspect: Primary erect, axillary acute angle to stem. Length of primary: Approximately 1.6 cm. Diameter of primary: Approximately 1.0 mm. Length of axillary: Approximately 1.2 cm. Diameter of axillary: Less than 1.0 mm. Texture: Moderately pubescent. Color: Closest to but redder than 200D.

Flower description:

*Type.*—Single.

*Bud.*—Rate of opening: Generally takes 3 to 5 days for bud to progress from first color to fully open flower.

*Bud just before opening.*—Shape: Ellipsoid to obovoid. Length: Approximately 13.0 mm. Diameter: Approximately 4.0 mm. Color: 92C, immature calyx colored 143A.

*Corolla.*—Shape: Salverform. Aspect: Facing upright and outward. Length: Approximately 1.4 mm. Diameter: Approximately 2.3 mm.

*Petals.*—Quantity: 5, lower half of petals fused into a narrow tube. Shape: Obovate. Margin: Entire. Apex: Deeply emarginate, forming two lobes each having obtuse apex. Length of free portion: Approximately 1.1 cm. Width: Approximately 9.0 mm. Color of upper surface when first open: 91B, with two small spots of N92D at corolla tube opening. Color of lower surface when first open: 85C. Color of upper surface when fully open: 91B to 91C, with two small spots of N92D at corolla tube opening. Color of lower surface when fully open: 85C.

*Corolla tube.*—Length: Approximately 1.2 cm. Diameter at distal end: Approximately 2.0 mm. Diameter at proximal end: Approximately 1.2 mm. Texture of inner and outer surfaces: Glabrous. Color of inner surface: N92B with 93C. Color of outer surface: N92D.

*Calyx.*—Shape: Campanulate. Length: Approximately 7.0 mm. Diameter: Approximately 5.0 mm.

*Sepals.*—Quantity per flower: 5, base fused. Shape: Linear. Apex: Narrow apiculate. Length: Approximately 6.0 mm. Width: Approximately 1.2 mm. Texture of inner surface: Glabrous. Texture of outer surface: Sparsely pubescent with very short glandular hairs. Color of inner surface: 147B. Color of outer surface: 147B, strongly tinted with darker than 197A.

*Pedicel.*—Strength: Strong, flexible. Aspect: Primary erect, axillary acute angle to peduncle. Length: Approximately 1.2 cm. Diameter: Less than 1.0 mm. Texture: Smooth, glabrous. Color: Closest to but redder than 200D.

*Reproductive organs.*—Androecium: Stamen quantity: 5 per flower. Stamen length: Approximately 1.0 cm. Anther shape: Oblong, basifixed. Anther color: 156D. Pollen amount: Sparse. Pollen color: 14A. Gynoecium: Pistil quantity: 1 per flower. Pistil length: Approximately 8.5 mm. Stigma shape: Cleft, three-parted. Stigma color: 154C. Style length: Approximately 7.0 mm. Style color: 154C to 154D. Ovary color: 143A.

Seed and fruit production: Neither seed nor fruit production has been observed.

Disease and pest resistance: Resistance to pathogens and pests common to *Phlox* has not been observed.

What is claimed is:

1. A new and distinct cultivar of *Phlox* plant named 'Florphfabv', substantially as herein illustrated and described.

* * * * *